United States Patent [19]

Kan et al.

[11] Patent Number: 4,508,720

[45] Date of Patent: Apr. 2, 1985

[54] AMINO DERIVATIVES OF PYRIDAZINE, AND COMPOSITIONS THEREOF FOR THE CENTRAL NERVOUS SYSTEM

[75] Inventors: Jean-Paul Kan; Kathleen Biziére, both of Clapiers; Camille G. Wermuth, Strasbourg, all of France

[73] Assignee: Sanofi, Paris, France

[21] Appl. No.: 402,906

[22] Filed: Jul. 29, 1982

[30] Foreign Application Priority Data

Aug. 7, 1981 [FR] France ............... 81 15380

[51] Int. Cl.$^3$ ............... A61K 31/50; C07D 237/20
[52] U.S. Cl. ............... 514/247; 544/224
[58] Field of Search ............... 544/224; 424/250

[56] References Cited

FOREIGN PATENT DOCUMENTS 1345880 2/1974 United Kingdom .

*Primary Examiner*—Glennon H. Hollrah
*Assistant Examiner*—Springer D. B.
*Attorney, Agent, or Firm*—Scully, Scott, Murphy & Presser

[57] ABSTRACT

The present invention relates to amino derivatives of pyridazine of general formula:

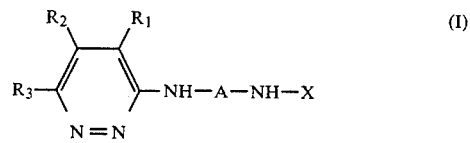

in which
one of the substituents $R_1$, $R_2$ or $R_3$ represents a phenyl or hydroxyphenyl group, while the other two represent hydrogen or an alkyl group with $C_1$–$C_4$;
A represents a linear or branched alkylene group having 2 to 5 carbon atoms;
X represents hydrogen or an alkyl group with $C_1$–$C_4$, as well as the salts of said derivatives with the pharmaceutically acceptable acids, and also relates to a process for preparing the products of formula (I) and to drugs containing a product of formula (I).

3 Claims, No Drawings

AMINO DERIVATIVES OF PYRIDAZINE, AND COMPOSITIONS THEREOF FOR THE CENTRAL NERVOUS SYSTEM

For numerous years, derivatives of pyridazine have been proposed as drugs. In a large number of cases, these are substances active on the cardiovascular system, presenting in particular an antihypertensive or vasodilator effect. More rarely, an anti-inflammatory and analgesic action has been mentioned among pyridazine derivatives. Finally, French Pat. No. 2 141 697 describes a family of products of general formula:

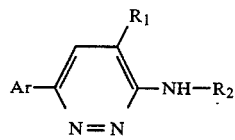

where $R_1$ represents hydrogen or a lower alkyl group
Ar represents an aromatic radical
$R_2$ designates a group

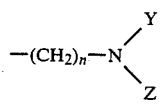

in which n=2 or 3 and Y and Z represent a lower alkyl group or

constitutes a heterocyclic radical.

These compounds are characterised by a psychotherapeutic action of psychotonic type.

A subsequent study of the compound where $R_1=CH_3$, Ar=phenyl and

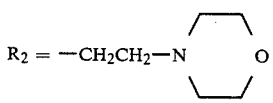

which received International Common Denomination "minaprine", showed that it is question of a psychotherapeutic action of a novel type which has been designated by "disinhibitory" activity. Furthermore, at a dose higher than 100 mg/kg per os, this product proves convulsivant.

It has now been found that certain 3-amino pyridazines have the same pharmacological properties as minaprine, whilst being less toxic and having virtually no convulsivant action.

The present invention relates to a family of amino compounds derived from pyridazine of general formula:

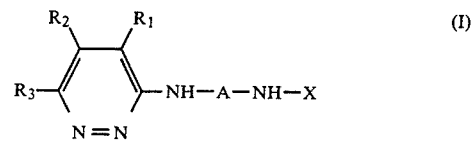

in which
one of the substituents $R_1$, $R_2$ or $R_3$ represents a phenyl or hydroxyphenyl group, whilst the other two represent hydrogen or an alkyl group with $C_1-C_4$;

A represents a linear or branched alkylene group having 2 to 5 carbon atoms;

X represents hydrogen or an alkyl group with $C_1-C_4$.

The present invention also relates to the addition salts which the compounds (I) furnish with the pharmaceutically acceptable acids. It also comprises a process for preparing the compounds of formula (I) and their salts as well as application thereof in therapeutics.

The compounds according to the invention are obtained from a suitably substituted 3-chloro pyridazine (1) by action of an amine $H_2N-A-NH-X$ according to the following scheme:

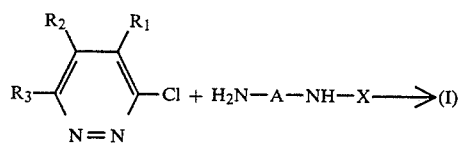

Reaction between the chlorinated derivative 1 and the amine 2 is generally effected by heating within a suitable solvent such as an alcohol, most often at boiling temperature of the solvent. The duration of the reaction varies from a few hours to several days depending on the nature of the reagents employed. When the reaction proves to be too slow, it may be catalyzed by adding a small quantity of powdered copper.

Reaction is effected in the presence of a hydracid acceptor adapted to fix the hydrochloric acid formed; an excess of the amine 2 is most often used as such.

Isolation of compound (I) is effected by taking up in water and extraction with a suitable solvent such as ethyl acetate.

Compounds (I) may be salified in conventional manner by action of the acid on a hot solution of the base, the solvent being chosen so that the salt crystallizes by cooling.

The 3-chloro pyridazines used as starting product are obtained by the corresponding 2H 3-pyridazones by action of an excess of phosphorus oxychloride. The 2H 3-pyridazones of which certain are known may be obtained by known processes such as the action of hydrazine on the γ-ketonic acids or activated derivatives thereof.

The following non-limiting examples are given by way of illustration of the present invention.

EXAMPLE 1

3-(2-Amino Ethylamino)4-Methyl 6-Phenyl Pyridazine(Hydrochloride)—(CM 30099)

(I) $R_1 = CH_3$ $R_2 = H$ $R_3 = $ 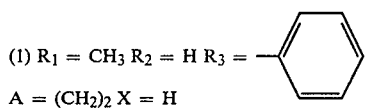

$A = (CH_2)_2$ $X = H$

The mixture of 4.1 g of 3-chloro 4-methyl 6-phenyl pyridazine and 10 g of 1,2-diamino ethane is heated to reflux in an inert atmosphere (argon).

The progress of the reaction is followed by taking a sample of the reaction mixture subjected to thin layer chromatography.

When the chlorinated derivative has totally disappeared, the excess amine is evaporated to dryness. To eliminate the last traces of amine, the residue is taken up twice in ethanol and evaporated to dryness.

Hydrochloride: The hygroscopic base thus obtained in dissolved in methanol and 1.1 equivalent of gaseous hydrochloric acid is added. By addition of anhydrous ether, the hydrochloride precipitates. It crystallizes with 3 molecules of water. m.p.: 255° C.

By operating in the same manner but by replacing the 1,2-diamino ethane by 1,3-diamino propane, 3-(3-amino propylamino)4-methyl 6-phenyl pyridazine (CM 30486) is obtained, a hygroscopic white powder isolated in the form of dihydrochloride crystallizing with one molecule of water. m.p.: 160° C. with decomposition.

Similarly, with 1,4-diamino butane,3-(4-amino butylamino)4-methyl 6-phenyl pyridazine (CM 30487) is obtained, a hygroscopic white powder isolated in the form of dihydrochloride crystallizing with one molecule of water. m.p.: 150° C. with decomposition.

EXAMPLE 2

2-(2-Methylamino Ethylamino)4-Methyl 6-Phenyl Pyridazine (SR 95029)

Operation is carried out as in Example 1, replacing the 1,2-diamino ethane by an equivalent quantity of 1-amino 2-methylamino ethane.

By the same treatment, the expected product is obtained, isolated in the form of dihydrochloride; m.p.: 252° C.

EXAMPLES 3 TO 6

By operating as in Example 1, but by varying on the one hand the substituents of the 3-chloro pyridazines 1 and/or on the other hand the diamines 2 used as starting products, the various compounds (I) shown in Table I are obtained.

TABLE I

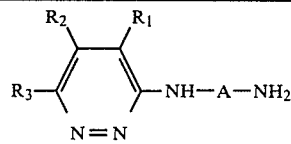

| Code No. | $R_1$ | $R_2$ | $R_3$ | A | Salt Melting point °C. |
|---|---|---|---|---|---|
| SR 95002 | 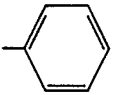 | H | H | —(CH$_2$)$_2$— | Dihydrochloride (1 Mole water) m.p.: 191° C. |
| SR 95030 | —CH$_3$ | H | 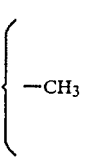 | —CH$_2$—CH— $\vert$ CH$_3$ —CH—CH$_2$— $\vert$ CH$_3$ | Mixture of the 2 isomers Dihydrochloride (½ Mole water) m.p.: 271° C. |
| SR 95085 | H | H | 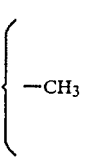 | —(CH$_2$)$_2$— | Dihydrochloride m.p.: 170° C. |
| SR 95086 | H | 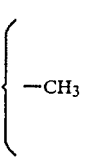 | H | —(CH$_2$)$_2$— | Dihydrochloride m.p.: 200° C. |

EXAMPLE 7

3-(2-Amino Ethylamino)4-Methyl 6-(4-Hydroxy Phenyl)Pyridazine(Dihydrobromide) (SR 95073)

(1) $R_1 = CH_3$; $R_2 = H$; $R_3 = HO$— 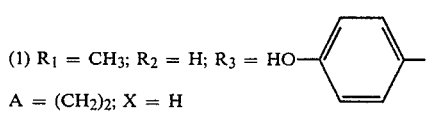

$A = (CH_2)_2$; $X = H$ (a) 2-(2-amino ethylamino)4-methyl 6-(4-methoxy phenyl) pyridazine Operation is carried out as in Example 1, replacing the 3-chloro 4-methyl 6-phenyl pyridazine by an equivalent quantity of 3-chloro 4-methyl 6-(4-methoxy phenyl) pyridazine. The expected product is obtained in oily form.

(b) SR 95073

The solution of 15 g of the product obtained hereinabove in 150 ml of a 2-1 (vol/vol) mixtures of 48% hydrobromic acid and acetic acid, is heated to reflux for 6 hours.

The product is evaporated to dryness. A brownish oil remains which crystallizes in the ethanol-ether mixture.

After recrystallization in aqueous ethanol, the dihydrobromide melts at 284° C.

The products according to the invention were subjected to pharmacological tests with a view to determining their activity on the central nervous system as well as the toxicity thereof.

ACUTE TOXICITY

The products to be studied were administered by the intraperitoneal route at increasing doses to batches of 10 mice. The mortality provoked by the products studied were noted during the 24 hours following administration of the product.

From the results obtained, the LD 50, i.e. the dose provoking the death of 50% of the animals studied, is determined for each of the products studied.

During the same experiments, the convulsivant threshold dose of the product is also noted, i.e. the minimum dose for which a convulsivant activity begins to be shown.

The results obtained are shown in Table II. Three products of the prior art are given in this Table by way of comparison:

TABLE II

Minaprine (DCI): phenyl-CH=C(CH₃)-pyridazine-NH—CH₂CH₂—N(morpholine)  where N=N

CM 30071: phenyl-CH=C(CH₃)-pyridazine-NH—CH₂CH₂—N(CH₃)₂, N=N

CM 30070: phenyl-CH=C(CH₃)-pyridazine-NH—CH₂CH₂—N(C₂H₅)₂, N=N

| Compounds | Toxicity LD$_{50}$ (mg/kg; i.p.) | Convulsivant threshold dose (mg/kg; i.p.) |
|---|---|---|
| Minaprine | 63 (52–77) | 35 |
| CM 30070 | 80 (61–106) | 60 |
| CM 30071 | 118 (101–139) | 100 |
| CM 30099 | >200 | 200 |
| CM 30486 | >200 | >200 |
| CM 30487 | >200 | >200 |
| SR 95002 | ≃150 mg/kg | 100 |
| SR 95029 | >200 | 200 |
| SR 95030 | >200 | >200 |
| SR 95073 | >200 | >200 |
| SR 95085 | >200 | >200 |
| SR 95086 | >200 | >200 |

The figures given in Table II show that the products according to the invention present a toxicity and convulsivant action much less than those of the reference products.

ANTIDEPRESSANT ACTIVITY

Despair reaction

This test was carried out in the female mouse, CDI (Charles River), weighing 18 to 23 g, according to the method described by Porsolt (Archives Internationales de Pharmacodynamie, 1977, 229, 327–336).

The principle of this test is as follows: when a mouse is placed in a narrow recipient, filled with water, it struggles, then, after 2 to 4 mins., it becomes still and floats on its stomach, its back rounded, its rear paws drawn up under its body and it makes only a few movements necessary for maintaining its head out of the water. This reaction is called the despair reaction.

Certain psychotherapeutic agents, particularly the antidepressants, extend the time during which the mouse struggles.

The following protocol was chosen: The products to be studied were administered by the i.p. route one hour before the test. For the test, the animals are placed in a narrow recipient (10×10×10 cm), filled with water, up to a height of 6 cm, the temperature of the water being 24° C.±2° C. The animals are left 6 minutes in the water and the time when the animal remains immobile between the 2nd and the 6th minute is measured—the shorter this time, the more active the substance.

Each substance was studied on a batch of 10 mice. The results are the average of at least two experiments.

Antagonism of the ptosis induced by reserpine

This test, described by GOURET (Journal de Pharmacologie (Paris), 1973, 4 (1), 105–128), was made on the female mice CDI (Charles River), weighing 20±1 g. The reserpine causes a ptosis one hour after intravenous administration thereof; certain antidepressants oppose this ptosis.

The following protocol was chosen:

The substances to be studied were administered by the i.p. route. The reserpine was administered simultaneously by the intravenous route at the dose of 2 mg/kg. One hour after administration of reserpine, the number of animals not presenting ptosis is noted.

This test was carried out on batches of 10 mice, the results are expressed in percentage of animals not presenting ptosis and are the average of at least two experiments.

The results obtained with the products of the invention are shown in Table III. By way of comparison, the results obtained with the three products of the prior art, Minaprine, CM 30070 and CM 30071 have also been indicated.

TABLE III

| | Antidepressant activity | |
|---|---|---|
| Compounds | Antagonisme of ptosis induced by reserpine | Behavioral Despair |
| Minaprine | ED$_{50}$ = 5 mg/kg (4–7) | 10 mg/kg: −35%** |
| CM 30070 | ED$_{50}$ ≃ 50 mg/kg | 25 mg/kg: inactive |
| CM 30071 | ED$_{50}$ ≃ 50 mg/kg | 10 mg/kg: inactive |
| CM 30099 | ED$_{50}$ = 16 mg/kg (14–18) | 10 mg/kg: −50%** |
| CM 30486 | ED$_{50}$ ≃ 10 mg/kg | 10 mg/kg: −20%* |

From Tables I, II and III, it is clear that the compounds representative of the present invention have, overall, an antidepressant activity of the same order of size as that of minaprine.

With respect to minaprine and especially to CM 30070 and CM 30071, the products representative of the present invention are very slightly toxic and have virtually no convulsivant activity.

The new compounds of the present invention may thus be used in therapeutics for all disorders in phychomotor behaviour.

They may be prescribed inter alia in the masked depression of the adult, in serious depressive states, in the depression of the elderly as in disorders in the memory and in senescence. These products may be administered by the oral route or by the injectable route. The pharmaceutical compositions may be solid or liquid and be in the form of tablets, capsules, granulates, suppositories, or injectable preparations.

Dosage may vary to large proportions in particular depending on the type and seriousness of the disorder to be treated and depending on the mode of administration. In the adult, by the oral route, it is most often between 0.010 g and 0.500 g, possibly distributed in several doses.

The following Galenic preparation may be indicated by way of example:

| CAPSULES | |
|---|---|
| CM 30099 | 100 mg |
| Aerosil | 0.5 mg |
| Magnesium stearate | 1.5 mg |
| Starch STA RX 1500 | 48 mg |

| -continued | |
|---|---|
| CAPSULES | |
| | 150 mg |

What is claimed is:

1. An amino derivative of pyridazine of the general formula:

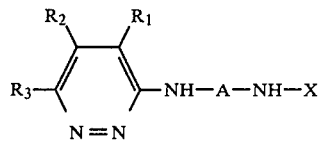

wherein:
$R_1$ is selected from the group consisting of hydrogen and a lower alkyl group having from 1 to 4 carbon atoms;
$R_2$ is hydrogen;
$R_3$ is selected from the group consisting of a phenyl group and a hydroxyphenyl group;
A is a linear or branched alkylene group having 2 to 5 carbon atoms; and
X is selected from the group consisting of hydrogen and a $C_1$–$C_4$ alkyl group, as well as the salts of said derivatives with the pharmaceutically acceptable acids.

2. A pharmaceutical composition useful in the treatment of psychomotor behavioral disorders comprising an effective amount of a compound within the scope of claim 1 and a pharmaceutically acceptable carrier.

3. The pharmaceutical composition of claim 6 wherein the compound is present in an amount from 0.01 to 0.500 g.

* * * * *